United States Patent [19]

Uhlen

[11] Patent Number: 5,405,746

[45] Date of Patent: Apr. 11, 1995

[54] METHOD OF SEQUENCING DNA

[75] Inventor: Mathias Uhlen, Uppsala, Sweden

[73] Assignee: Cemu Bioteknik AB, Uppsala, Sweden

[21] Appl. No.: 124,628

[22] Filed: Sep. 22, 1993

Related U.S. Application Data

[63] Continuation of Ser. No. 865,656, Apr. 7, 1992, abandoned, which is a continuation of Ser. No. 572,945, filed as Pct/GB89/00304, Mar. 22, 1989, abandoned.

[30] Foreign Application Priority Data

Mar. 23, 1988 [SE] Sweden ................. 8801070

[51] Int. Cl.$^6$ .................. C12Q 1/68; C12P 19/34
[52] U.S. Cl. .................... 435/6; 435/91.2; 935/77; 935/78
[58] Field of Search ............ 435/6, 91.1, 91.2

[56] References Cited

U.S. PATENT DOCUMENTS

| 4,734,363 | 3/1988 | Dattagupta et al. | 435/6 |
| 4,851,331 | 7/1989 | Vary et al. | 435/91 |

FOREIGN PATENT DOCUMENTS

| 0206411 | 12/1986 | European Pat. Off. | 436/94 |
| 0224126 | 3/1987 | European Pat. Off. | 435/91 |
| 0229701 | 7/1987 | European Pat. Off. | 435/6 |
| 0371437 | 6/1990 | European Pat. Off. | 435/6 |
| WO87/07645 | 12/1987 | WIPO | 435/6 |

OTHER PUBLICATIONS

Hartley et al., Nuc. Acids Res. 10 (13): 4009–4025 (1982).
Rosenthal et al., Nuc. Acids Res. 13 (4): 1173–1184 (1985).
*Nucleic Acids Research*, vol. 13, No. 15, pp. 5457–5469, 1985 "Separation of complementary strands of plasmid DNA using the biotin–avidin system and its application to heteroduplex . . . " Hajo Delius, et al.
*Methods in Enzymology*, vol. 155, pp. 301–331, 1987 "Solid–Phase Methods for Sequencing of Oligodeoxyribonucleotides and DNA" Andre Rosenthal, et al.
*Nucleic Acids Research, vol. 16 No. 7, pp. 3025–3039, Apr. 11, 1988, "Solid phase DNA sequencing using avidin system"* Stefan Stahl, et al.
*Nucleosides & Nucleotides,* vols. 7(5&6), pp. 629–638, 1988, "Approaches to Solid Phase DNA Sequencing", Thomas Hultman, et al.

Primary Examiner—Stephanie W. Zitomer
Attorney, Agent, or Firm—Foley & Lardner

[57] ABSTRACT

The invention relates to a method of sequencing target DNA in which said DNA is provided in double stranded form immobilized on a solid support via one terminus of one of the two strands thereof and is then subjected to strand separation whereby the unattached strand is removed prior to sequencing the immobilized strand. The target DNA, e.g genomic DNA, may initially be amplified by the PCR method using at least one oligonucleotide primer which is either attached to a solid support or carries means for attachment to a solid support.

13 Claims, 6 Drawing Sheets

METHOD OF SEQUENCING DNA

This application is a continuation of application Ser. No. 07/865,656, filed Apr. 7, 1992 and now abandoned which is a continuation of application Ser. No. 07/572,945, filed PCT/GB89/00304, Mar. 22, 1989, and now abandoned.

The invention is related to a method of sequencing DNA using a solid phase bound DNA template.

The increased interest in large scale sequencing projects, such as proposals to sequence the entire human genome (Smith et al (1987)), necessitates technical improvements to enable megabase sequencing. Sequencing can be divided into the following five operations, which all must be automated to enable large scale projects: (i) template preparation, (ii) sequence reactions, (iii) electrophoresis, (iv) detection of specific fragments and (v) data storage and analysis. Except of data storage and analysis, most sequencing is at present carried out manually, causing considerable investments in operator time.

Recently, many technical improvements have been reported, although the major contributions concern the data evaluation, i.e. computer software. A filter method to perpare single stranded phage DNA has been described (Kristnesen et al (1987)), which may be developed into an automated procedure. Attempts to develop automated sequencing reactions by a centrifugal reagent handling device have also been described (Martin et al (1985)) as well as image processing programs for the detection of the bands on the radiograms (Elder et al (1985)). However, the most common approach has been to automate techniques with the aid of robots. Using such a strategy, systems for high-speed sequencing (Wada et al 1983)) and DNA template preparations (De Bonville et al 1987)) have been introduced.

A novel approach to automize the electrophoresis step has been described by several groups (Smith et al (1986), Ansorge et al (1987) and Prober et al (1987)) taking advantage of fluoresence instead of isotopes for labelling the DNA fragments. With these systems online detection can be achieved, which makes it possible to combine the three operations electrophoresis, detection and data handling into a single automated station. Such systems are therefore likely to be included in megabase sequencing strategies.

To obtain a completely automated sequencing protocol, it is therefore essential to also develop suitable automated methods for the first two operations (template preparation and sequencing reactions). For the latter operation a strategy involving solid phase techniques would facilitate automated handling of liquids in microliter quantities, which would be suitable for automated protocols.

According to the present invention we provide a method of sequencing target DNA in which said DNA is provided in double stranded form immobilized on a solid support via one terminus of one of the two strands thereof and is then subjected to strand separation whereby the unattached strand is removed prior to sequencing the immobilized strand.

Solid phase methods have proven to be very useful in molecular biology, in areas such as peptide synthesis, peptide sequencing and DNA synthesis. A large number of instruments are commercially available utilizing this technique. The advantage with a solid phase approach is usually a combination of good yields, reproducable reactions and easy automation due to ease of separation of the solid phase from the reaction solution.

At present there are, however, few reports on solid phase approaches to handling manipulatations of cloned DNA sequences for applications such as DNA sequencing reactions. DNA sequencing of oligonucleotides on anion-exchange supports (Rosenthal et al, 1985) has been described, but most attempts to automate DNA sequencing have been focused on the use of laboratory robots (Martin et al, 1985, and Wada et al, 1987).

H. Delius et al (Nucleic Acids Research, Vol 13, No 15, 1985 p 5457) has described immobilisation of double stranded DNA and strand specific elution but only in the context of electron microscopic analysis of heteroduplexes.

In the preferred method of the present invention a desired DNA sequence is selectively incorporated into a double stranded plasmid or phage vector. A functional group with affinity for a certain substance is incorporated into the desired strand of the vector DNA. This substance is bound to a solid phase and when the vector is brought into contact with the solid phase it is immobilized via interaction between the functional group and the substance. The vector is then subjected to melting and the non-bound DNA strand is thereafter eluted under suitable conditions.

The double stranded DNA can be any vector, such as a plasmid or a phage, that can provide suitable cloning sites for incorporation of target DNA and also restriction sites for linearization. Two plasmid vectors especially designed and constructed for use according to the present invention are plasmids pRIT27 and pRIT28, described in the experimental part. However, phage vectors such as Lambda or cosmid vectors can also be used.

The desired DNA sequence could vary considerably in length, from a few base pairs up to a least 30–40 thousand base pairs, depending on the application. The DNA sequence is selectively incorporated into the vector using recombinant DNA techniques known per se.

The functional group could be any compound which can be incorporated into deoxynucleotides and which has a strong interaction to a substance which can be immobilized on a solid-support. The interaction between the two components must be stable through the whole procedure. Examples of such groups are biotin - avidin, biotin - streptavidin, and cystein - thiol groups.

Incorporation of the functional group A into the vector DNA must be performed in such a way that the functional site is not affected. One example of such a functional group for binding is 11-biotin-dUTP. The vector must be linearized, and this can be done by suitable restriction enzymes, such as BstEII, BglII (plasmid pRIT27) or NotI (pRIT28). Using lambda or cosmid vectors, it is possible to linearized the vector with a phage specific enzyme which recognizes and cleaves the cos-site, thus avoiding restriction enzymes.

The incorporation of the functional group can be accomplished by a DNA polymerase, such as Klenow, T7 or reverse transcriptase (Pharmacia, Sweden), if a 5'-protruding end exists after linearisation. It is also possible to incorporate the functional group into the vector by ligation with a suitable oligonucleotide synthesized with the functional group.

The immobilization process may be performed in a conventional manner, either batch-wise with the substance-coupled carrier slurried in a suitable medium or on a column of the activated carrier. Any conventional carrier material (such as beads e.g. Sepharose beads, (Pharmacia, Sweden)), filters, capillaries, or plastic dipsticks (e.g. polystyrene strips) and microtitre wells to which the substance can be sufficiently coupled for the present purposes, may be used. The methods for coupling or immobilizing a functional group to such carrier material are well-known and need not be described in any detail herein. It is also possible to use adsorption of the substance to surfaces of microtiter wells as a means for coating.

Release or melting of the non-bound DNA strand from the carrier material may be effected by conventional methods, such as 0.15M NaOH or temperature increase. The choice of melting conditions must, of course, be made with regard to the particular functional group-substance interaction as well as the choice of carrier material.

A valuable initial step in method of the present invention is thus to provide an immobilized single stranded recombinant DNA fragment suitable for DNA sequencing. An example of such a procedure is schematically outline in FIG. 1.

Briefly, the target DNA is cloned into the multilinker region of the sequencing vector. The plasmid is linearised with a restriction enzyme and the protrusions are filled in using deoxynucleotide(s) with at least one of them derivatized to contain the functional group. After restriction with a second enzyme, the mixture is contacted with a solid support containing a substance with affinity for the functional group. This leads to directed immobilization of the DNA fragments containing the functional group. Single stranded DNA is obtained by melting the strands, either by alkali or heat treatment, and simultaneous elution of the non-functional strand. A general sequencing primer is annealed to the resulting immobilized single stranded template and the sequencing reaction is performed under standard conditions (Sanger et al (1977)). The extended oligonucleotides can be labelled using different strategies, most notably isotopes or fluoresence which are incorporated either during the extension or as a labelled primer. The newly synthesized labelled oligonucleotides are eluted by another melting step leaving the template available for the next sequencing reaction. The annealing and extension is repeated to obtain specific fragments for all four nucleotides and the four samples are loaded on a sequencing gel.

Another useful element in the invention is the provision of templates for sequencing using biotinylated oligonucleotide and partial restriction enzyme cleavage reactions to obtain DNA fragments of different lengths with a biotin in one end of the fragment and an oligonucleotide complimentary to a sequencing primer in the other end. An example on such procedure is schematically outlined in FIG. 2.

Briefly, the target DNA is cloned into the multilinker region of the sequencing vector. The plasmid is linearized with SfiI and partially cleaved with Sau3A to yield fragments of different lengths. Two general oligonucleotides sfiI and Sau3A are ligated to the DNA fragments. The oligonucleotide that ligates to one of the SfiI recognized protruding ends carries the functional group and the oligonucleotide that ligates to the Sau3A protruding ends contains a primer annealing sequence. The mixture is separated by agarose or polyacrylamide gel electrophoresis and by using radioactive, fluorescent or alternative methods, fragments containing the SfiI oligonucleotide are visualized. The bands represent DNA fragments containing in one end of the oligonucleotide the functional group and in the other end the Sau3A oligonucleotide incorporated into a specific Sau3A site. After collecting the specific bands separately from the gel and eluting these by methods known per se, the DNA is immobilized by contact with a solid support containing a substance with affinity for the functional group. The sequencing is therefore carried out as described above (FIG. 1) except that a general sequencing primer (GSPIII) is used which is complimentary to the Sau3A oligonucleotide incorporated to the 3'-end of the immobilized fragment.

The advantage with this method is that large inserts (greater than 2000 base pairs) can be sequenced in a direct way without the need for subcloning of smaller framgments. It is of course possible to compliment the SfiI/Sau3A system with other enzymes such as TaqI, MspI, HpaII etc.

The immobilized single stranded DNA for sequencing may also be produced by the polymerase chain reaction (PCR) technique whereby relatively small amounts of the DNA to be sequenced, for example genomic DNA, can be greatly amplified enzymically and according to a modification, also immobilized an a solid support. In the PCR technique, two oligonucleotide primers are selected which hybridise to respective sequences at or near the 5'-ends of the coding and noncoding strands of the DNA to be amplified; after annealing to hybridise the primers to the target DNA, polymerisation is then effected using a suitable polymerase to produce a copy of each of the coding and noncoding strands incorporating the primers whereupon strand separation is effected, eg.g by conventional melting for example at 90° C. If an excess of the primer oligonucleotides is included in the medium as well as the four nucleotides required for synthesis, the separated new strands together with the original strands can serve as templates for a further cycle of annealing, polymerisation and strand separation. It will be seen that if this procedure is continued through a number of repeated cycles, the target DNA will be amplified exponentially while other DNA present will largely be unaffected. Recently, a thermophilic polymerase has become available, Taq 1, which can withstand the melting temperature needed for strand separation, thus. avoiding the need to add polymerase at each repeat of the cycle as when using the Klenow polymerase used originally in PCR.

If one of the oligonucleotide primers is attached to a solid support such as a particle or, more preferably, carries means permitting attachment to a solid support such as biotin, the amplified DNA will be produced with means for immobilisation. Thus, the PCR technique can produce directly immobilized single stranded DNA ready for sequencing and may produce this directly from a bacterial colony by a method which is easy to automate and does not involve restriction cleavages and plasmid purification. A particular advantage of the use of a solid support in any of the reactions here concerned is the ease of separation from the reaction medium. Thus, in the PCR stage, the reaction medium can be readily removed by washing and a different polymerase introduced in an optimal buffer to begin the sequencing stage, e.g. a conventional sequencing polymerase such as T7. Furthermore, the optimal concentrations of nucleotides and dideoxynucleotides can be maintained for sequencing by the Sanger method, independently of the concentrations used in the PCR step.

The possiblity of rigorous washing of the immobilized DNA provides more reproducible results in the sequencing stage. Furthermore, the so-called 'walking primer' technique is facilitated in Sanger sequencing whereby a primer can be used to sequence the first 500 base pairs of a long DNA molecule and after washing, the unchanged immobilized DNA is annealed to a primer initiating sequencing of the next 500 base pairs (using sequence information from the first stage), this procedure being continued until the whole DNA molecule has been sequenced.

The invention will in the following be further illustrated by non-limiting examples with reference to the appended drawings wherein.

Figure 3:
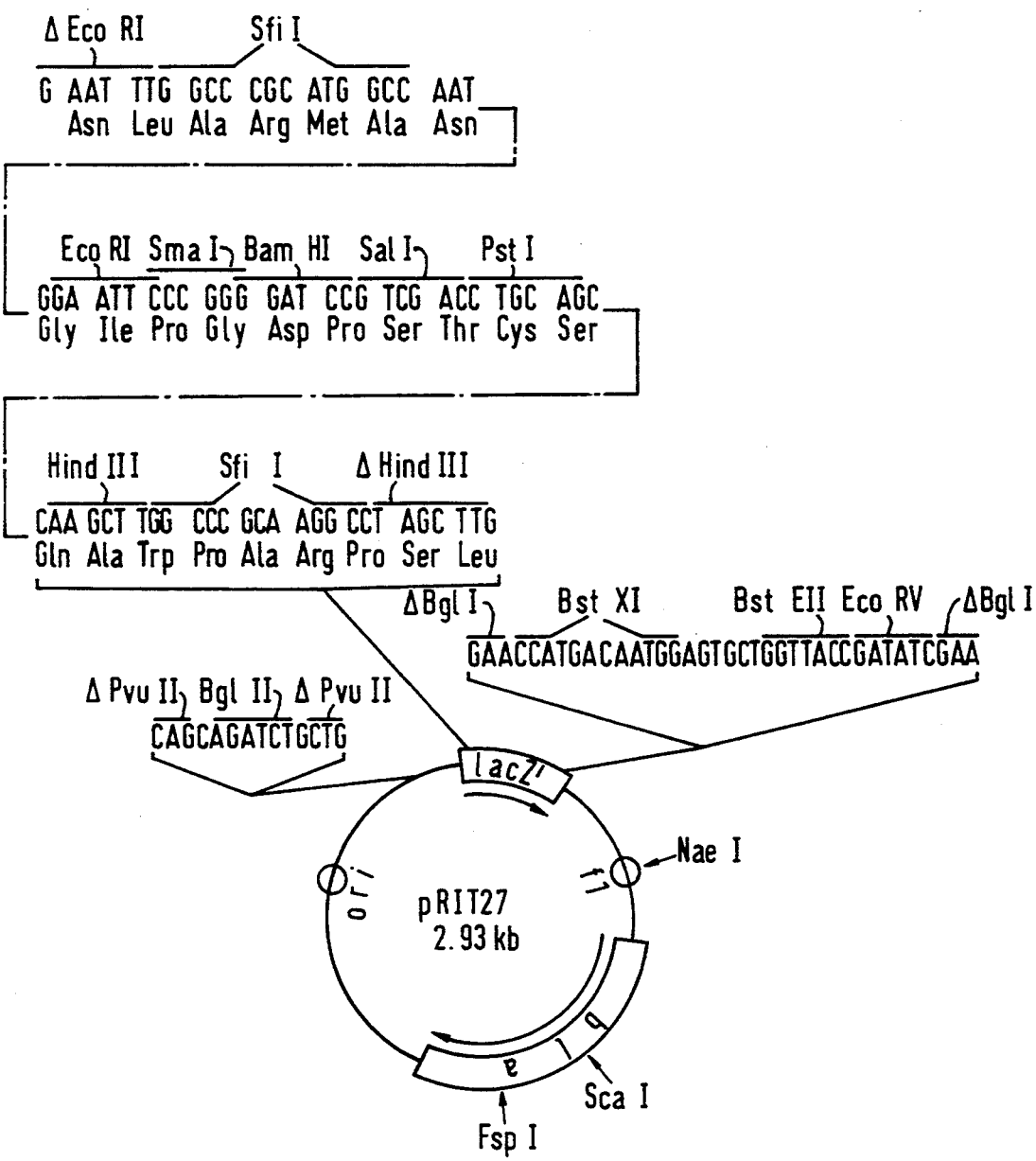

FIG. 3 shows the sequencing vector, pRIT27. The nucleotide sequence and the deduced amino acid sequence in the multi-linker region is shown as well as the sequence of the synthetic linkers inserted in the flanking regions. Abbreviations: bla, beta-lactamase gene; ori, origin of replication; fl, origin of replication of phage fl; lacZ', part of the beta-galactosidase gene.

Figure 4:
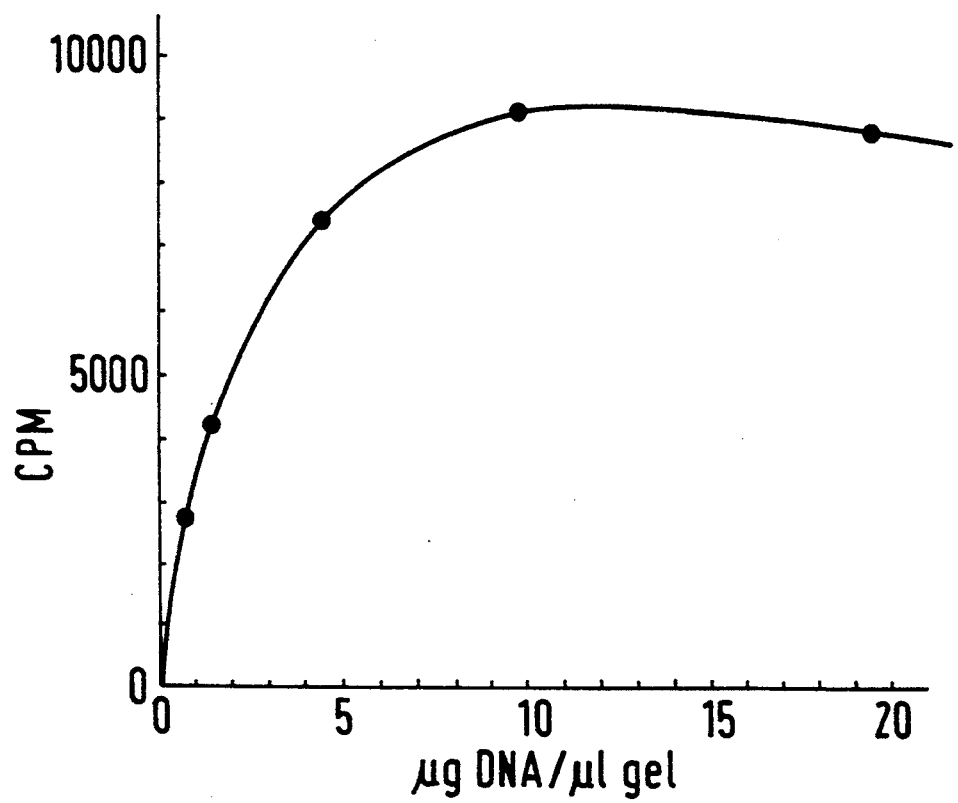

FIG. 4 shows the result of immobilization of biotinylized, double stranded pRIT27, end-labelled with $^{32}P$. The amount of label bound to 1 ul of avidin agarose after 30 minutes of incubation at room temperature is shown.

Figure 5:
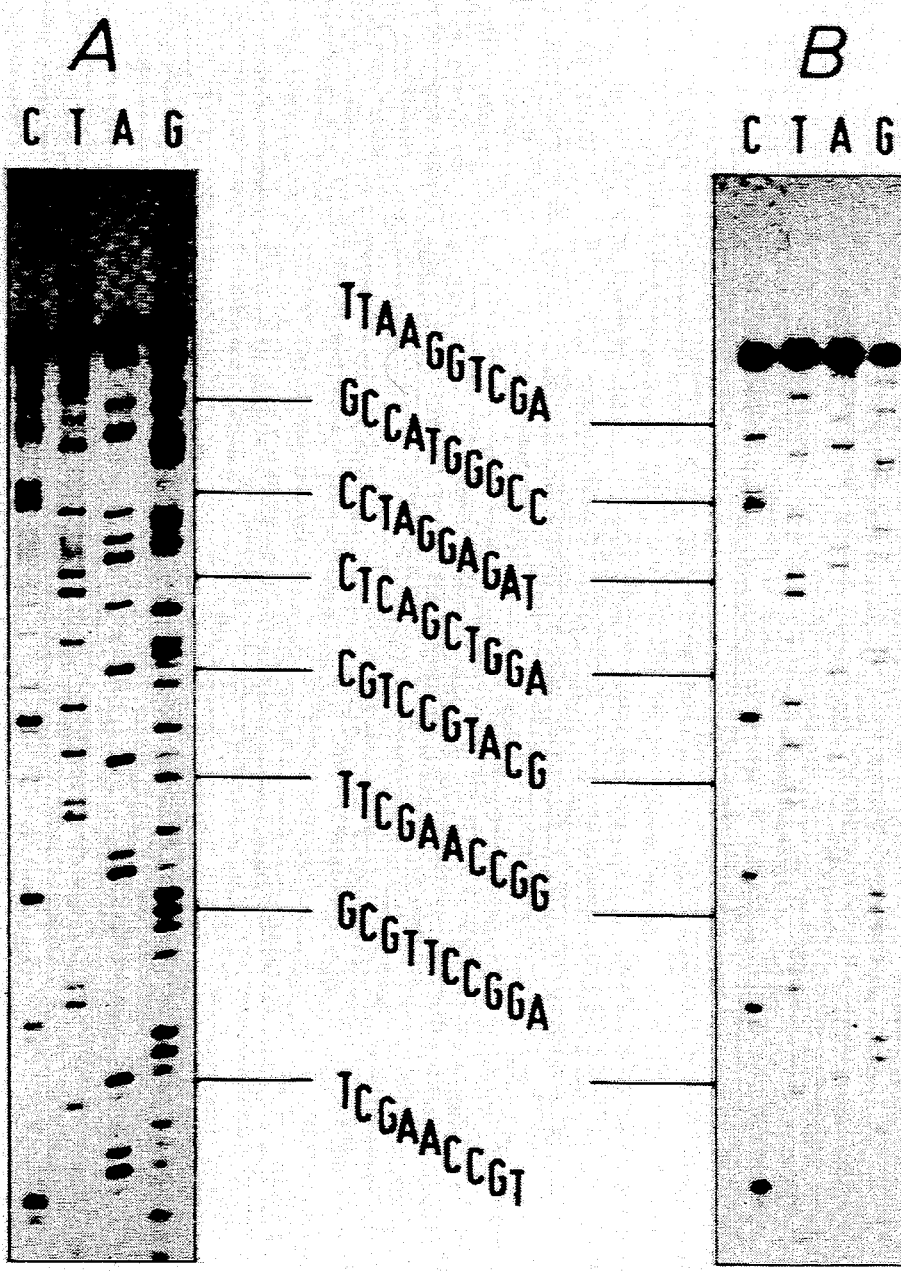

FIG. 5 shows the autoradiographs of sequencing gels with samples obtained by solid-phase sequencing. A; labelling using $^{35}S$-dATP during the extension. B; labelling using $^{32}P$ end-labelled sequencing primer. Also shown is the expected sequence.

Figure 6:
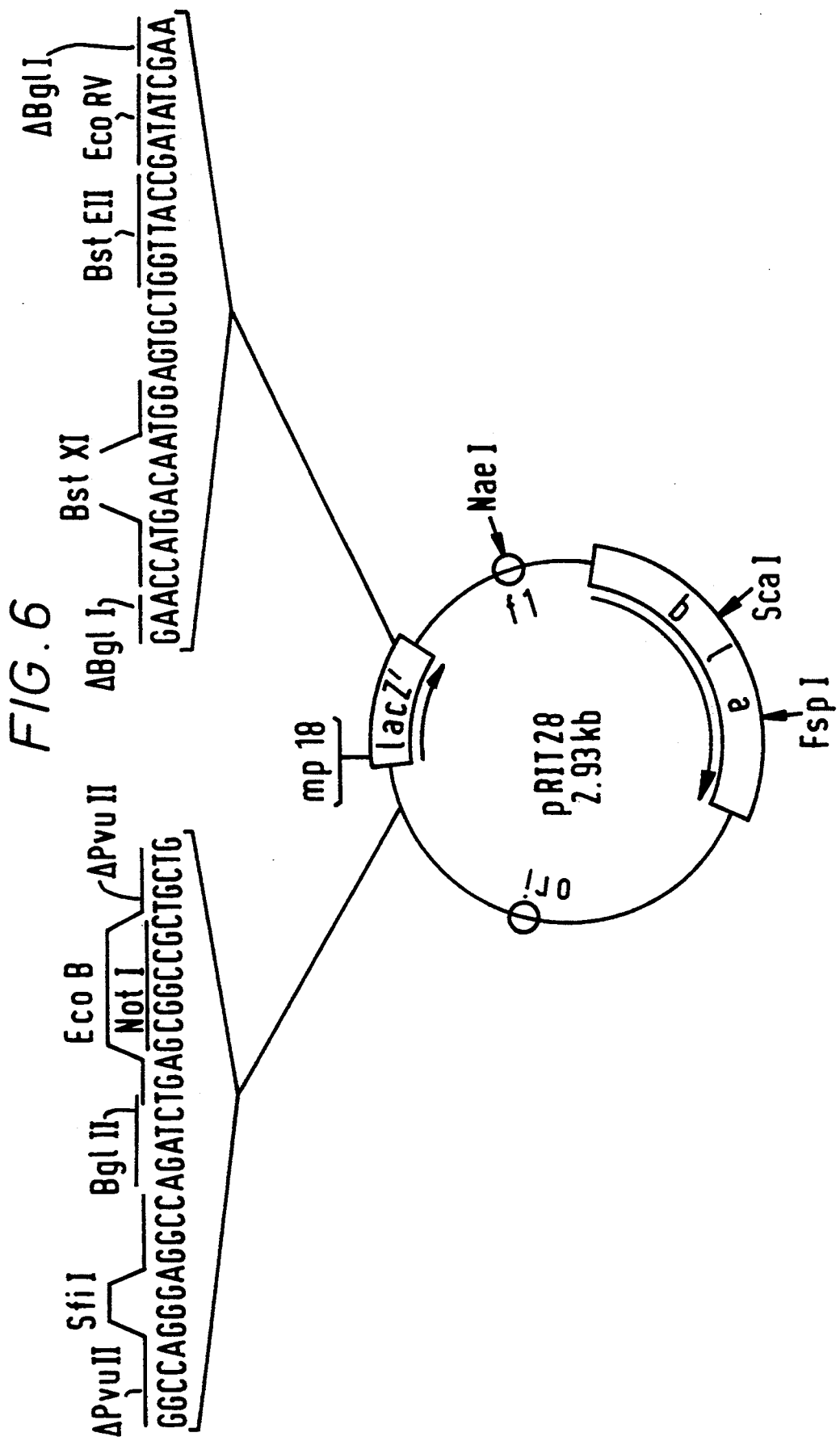

FIG. 6 shows the sequencing vector, pRIT28. The nucleotide sequence of the synthetic linkers inserted in the flanking regions a–e are shown. Abbreviations are as in FIG. 3.

Specific embodiments of the invention will now be described in detail.

MATERIALS AND METHODS

Enzymes were obtained from Parmacia Sweden, and were used according to the suppliers recommendations. DNA manipulations were according to standard procedures (Maniatis, 1982). 11-bio-dUTP was obtained from Bethesda Res. Labs. (US) and avidin agarose was obtained from Sigma Chemicals.

EXAMPLE 1

Construction of Plasmid pRIT27

Plasmid pTZ18 (Pharmacia AB, Sweden)) was partially digested with BglI and the synthetic oligonucleotide 5'-CCATGACAATGGAGTGCTGGTTACC-GATATCGAA-3' (and its complementary sequnce) was inserted. This synthetic fragment contains BstXI, BstEII and EcoRV recognition sequences. The BglI recognition sequence, used for the insertion, was destroyed simultaneously. The reading frame was changed in the last part of the lacz'-gene but the colour of the colonies remained blue, if E.coli strain RRI 15 (Maniatis et al (1982)) IPTG/X-gal, selection was used (Maniatis et al (1982)). This construction, designated pSS1, was digested with EcoRI and HindIII, and a synthetic oligonucleotide 5'-AATTCGGCCAG-CACGGCCGGCTCAGGTGACCA-3' was inserted. The EcoRI and HindIII sites were thus destroyed and a sequence of SfiI, EcoRI, PstI, HindIII, SfiI sites were created. This insertion changed the colour of the colonies from blue to white, due to fram-shift in the lac Z'-gene. The new EcoRI and HindIII recognition sequences were used to insert a mp 8 multi-linker, restoring the correct frame in the lac Z'-gene giving back blue colonies. Thereafter the PvuII site upstream of the lac Z'-gene was converted into a BglII site, by insertion of a linker 5'-CAGATCTG-3' (Kabigen, Sweden). The resulting plasmid was denoted pRIT27. (FIG. 3.)

Immobilization of Biotinylated Double Stranded DNA

Plasmid pRIT27 containing an insert derived from the multi-linker region of M13 mp 18, was digested with BstEII and EcoRV. The 5' protrusions were filled in with Klenow polymerase (Maniatis et al (1982)) using 11-bio-dUTP and appropriate dNTP's. The material was purified by passing it through a G-50 column, followed by ethanol precipitation. After redissolving in TE (10 mm TRIS pH 7.5, 1 mM EDTA) the plasmid was digested with EcoRI. This biotynlated double stranded DNA was mixed with avidin agarose gel, prepared by washing with 1M NaCl and TE. Approximately 1 ug of plasmid (treated as described above) was used per ul avidin agarose gel for the immobilization. The mixture was shaken gently at room temperature for one hour.

The capacity of the avidin agarose was determined by a saturation experiment. Avidin agarose was mixed with increasing amounts of labelled and biotinylated plasmid DNA and the amount of immobilized labelled material was determined. The result (FIG. 4) demonstrates that several ug of DNA can be bound to each ul of avid agarose, suggesting that the capacity of the matrix is sufficiently high to allow sequencing reactions in a reasonable scale.

Sequencing Reactions Using Immobilized Template DNA

The immobilized biotinylated double stranded DNA was converted into single stranded form by incubation at 37° C. with 0.15M NaOH for 15 minutes. The avidin agarose gel, with immobilized template DNA was subsequently washed with 0.15M NaOH and water. Sequencing reactions were performed using both $^{35}S$ labelled dATP and $^{32}P$ end labelled primer. In both case of 1 ug of the plasmid immobilized on 1 ul avidin agarose gel were mixed with equimolar amounts of the primer in a buffer, containing 10 mM Tris HCl (pH 7.5) 10 mM $MgCl_2$, 100 ug/ml BSA and 100 mM NaCl at a total volume of 10 ul. The mixture was incubated for 1 h at 60° C. and allowed to cool to room temperature. The supernatant was removed and the above described buffer, with addition of 1 ul BSA (1 mg/ml), was added, together with 1 ul Klenow polymerase and 5 ul of the respective nucleotide mix; for the $^{35}S$ protocol was 0.5 ul $^{35}S$-dATP (12.5 uCi/ul) also added. In both cases the reaction mixtures, at a total volume of 10 ul, were incubated 20 min at 37° C.

For the $^{35}S$ protocol the following nucleotide mixes were used.

Amix: 62.5 uM dCTP, dGTP, dTTP; 25 uM ddATP.
Cmix: 83 uM dGTP, dTTP; 4 uM dCTP; 50 uM ddCTP.

Gmix: 83 uM dCTP, dTTP; 4 uM dGTP; 150 uM ddGTP.

Tmix: 83 uM dCTP, dGTP: 4 uM dTTP; 125 uM ddTTP.

For the $^{32}$p-labelled primer the following nucleotide mixes were used.

Amix: 83 uM dCTP, dGTP, dTTP; 4 uM dATP; 50 uM ddATP.

Cmix: 83 uM dATP, dGTP, dTTP; 4 uM dCTP; 50 uM ddCTP.

Gmix: 83 uM dATP, dCTP, dTTP; 4 uM dGTP; 50 uM ddGTP.

Tmix: 83 uM dATP, dCTP, dGTP; 4 uM dTTP; 50 uM ddTTP.

After completed reactions the supernatant was removed and the gel was extensively washed with water. The newly synthesized oligonucleotides were eluted using 10 ul 0.15M NaOH and the eluant was subsequently neutralized with 1.25M HAc. The samples were ethanol precipitated and redissolved in 5 ul TE. A fraction of 2 ul was mixed with 2 ul formamide/dye mix and heated for 3 min in boiling water and loaded on gel a 6% polyacrylamide sequencing gel. The avidin agarose gel, with immobilized template DNA, was regenerated by extensive washing with 0.15M NaOH and water.

Solid-Phase Sequencing Using Labelled Deoxy-Nucleotide

The sequencing reactions were performed using a protocol involving labelling of the specific fragments with $^{35}$S during extention. A nucleotide mix was used containing, in addition to the standard nucleotides, the $^{35}$S-labelled dATP and one of the dideoxy nucleotides. In this and the following experiments, a plasmid was used, consisting of pRIT27 containing an insert derived from the multi-linker region of M13 mp 18.

Approximately 1 ug of the plasmid was used for the immobilization to 1 ul avidin agarose and the subsequent strand specific elution was performed as described above. A RIT primer (Olson et al, 1986), complimentary to a region immediately downstream from the multi-linker region, was used to initiate the extensions. Equimolar amounts of immobilized single stranded DNA and RIT primer were mixed, incubated for 1 hour at 60° C. and allowed to cool to room temperature. The supernatant was removed and the primer extension was started with the appropriated nucleotide mix in a total volume of 10 ul, followed by a chase reaction (Sanger et al (1977)) to extend fragments not terminated with a dideoxy nucleotide.

After completion of the reactions, the supernatant was removed and the gel was extensively washed. The newly synthesized oligonucleotides were then eluted using 0.15M NaOH and the eluant was neutralized with HAc. The affinity gel containing the single stranded template was thereafter used for another round of sequencing reactions, involving primer annealing followed by extension using a new dideoxy nucleotide mix.

The protocol was followed for all four dideoxy nucleotides and the eluted samples were ehtanol precipitated and re-dissolved in formamide/dye mix prior to loading a sequencing gel. An autoradiogram of DNA fragments separated by electrophoresis is presented in FIG. 5A, which also shows the expected sequence of the plasmid used. Clearly readable sequences are obtained, which correlates well with the expected ones. The strong band at the top of the sequence represents run off transcripts at the EcoRI site at the 5' end of the immobilized template.

Solid-Phase Sequencing With End-Labelled Primer

An alternative strategy was also tested, using a $^{32}$P end-labelled RIT primer was used to label the extended DNA fragments. A similar protocol was used, although the nucleotide mixes were adjusted appropriately (see Materials and Methods for details). Different molar ratios of immobilized template and primer were tested. Equimolar amounts of template and primer (FIG. 5B) gave a clear and easily readable autoradiogram. Similar results were obtained for other primer/template ratios (data not shown), suggesting that the ratio can be varied without critically influencing the pattern.

Figure 1:
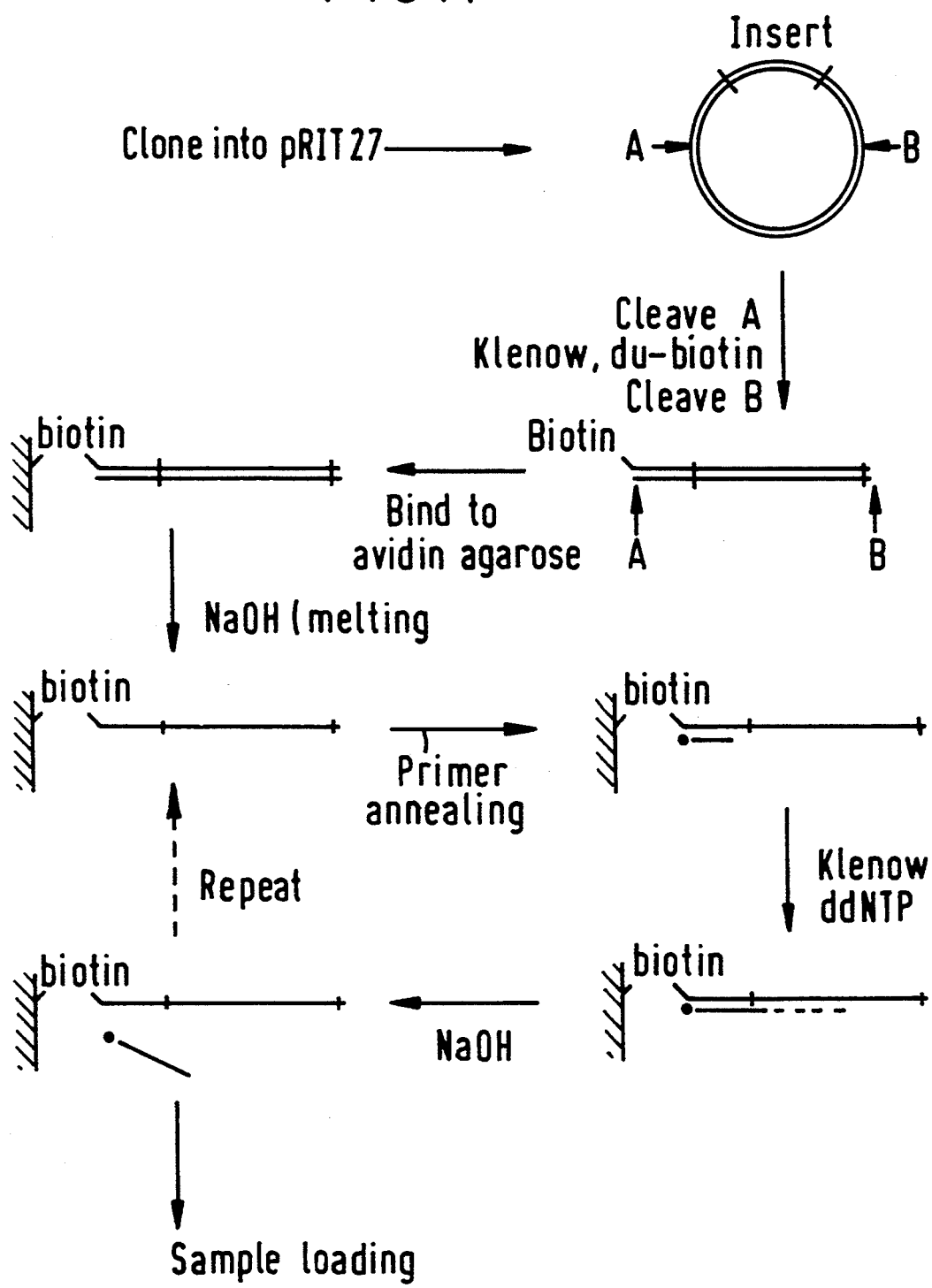
FIG. 1 is a schematic drawing of the basic concept of the solid-phase sequencing using the biotin-avidin system. Note that depending on the choice of enzymes A and B, both fragments will or will not be immobilized.

The results shown in FIG. 5 demonstrate that the strategy outline in FIG. 1 can be used for solid-phase DNA sequencing using the biotin-avidin system.

EXAMPLE 2

Construction of Plasmid pRIT28

Plasmid pSS1 (see above) was partially digested with PvuII and a synthetic oligonucleotide linker 5'-GGCCAGGGAGGCCAGATCT-GAGCGGCCGCTGCTG-3' (and its complimentary sequence) was inserted. This fragment contains SfiI, BglII, EcoB and NotI recognition sequences. The PvuII site used for the insertion was destroyed simultaneously. The resulting plasmid denoted pRIT28 (FIG. 6), is suitable for solid-phase sequencing using the approach outline in FIG. 2.

Ligation of Specific Oligonucleotides to Linearized pRIT28

Figure 2:
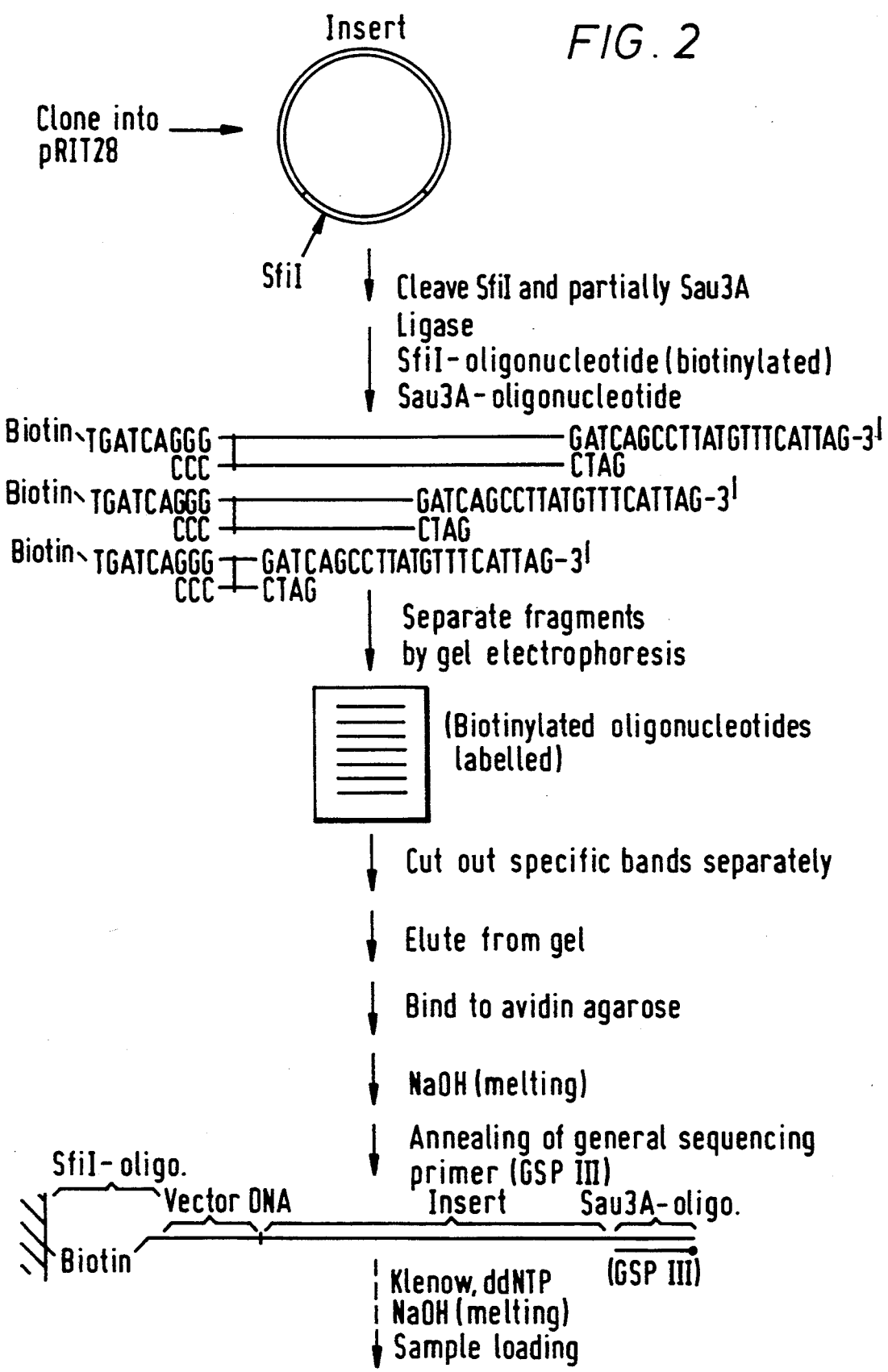
FIG. 2 is a schematic drawing of the basic concept to use a biotinylated oligonucleotide to sequence fragments obtained after partial cleavage with a restriction enzyme such as Sau3A.

A crucial step in the strategy outline in FIG. 2 is the ligation of specific oligonucleotides to plasmid DNA linearized with enzymes giving a 3'protruding end (such as SfiI, BstNl etc) and 5' protruding end (such as Sau3A, TaqI etc). To test the efficiency of ligation, two synthetic oligonucleotides were synthesized and ligated to pRIT28 cleaved with SfiI or BamHl. The synthetic SfiI oligonucleotide (5'-TGATCAGGG-3') is in the 3'-end complimentary to one of the strands of pRIT28 after cleavage with SfiI, while the synthetic BamHl oligonucleotide (5'-GATCAG CCTTATGTTCATTAG-3') is in the 5'-end complimentary to the 5'-protruding ends of DNA cleaved with Sau3A, BamHl etc.

To test the efficiency of ligation of each oligonucleotide to pRIT28, the ligation mixture was analyzed by 1% agarose gel electrophoresis, before and after ligation. A successful incorporation of oligonucleotide in the DNA vector will terminate further ligation between plasmids or circularization of plasmids. This can be observed by comparing the agarose gel pattern of ligation mixtures.

The synthetic Sau3A oligonucleotide (3'-GATTAC TTTGTATTCCGACTAG-5') was kinased with T4 polynucleotide kinase in a kinase buffer containing 50 mM Tris pH 8, 50 mM MgCl$_2$, 100 mM DTT and 10 mM ATP. 500 ng of pRIT28 was digested with BamHl and mixed with approx. 150 ng of the kinased oligonucleotide. The mixture was incubated at 14° C. over night with ligase and a buffer containing 40 mM Tris pH 7.4, 10 mM MgCl$_2$, 1.0 mM DTT and 0,2 mM ATP. After incubation the mixture was loaded on a 1% agarose gel.

Also 100 ng of the synthetic SfiI oligonucleotide (5'-TGATCAGGG-3') was mixed with 500 ng of pRIT28 digested with SfiI. The mixture was incubated at 14° C. over night with ligase in a buffer containing 40 mM Tris pH 7.4, 10 mM MgCl₂, 1.0 mM DTT and 0.2 mM ATP. After incubation the mixture was loaded on a 1% agarose gel.

The results of the agarose gel electrophoresis are presented in Table 1, which shows the relative amount of vector separating as linearized plasmid.

TABLE 1

Relative amount of linearized plasmed pRIT28, as determined by 1% agarose gel electrophoresis, after cleavage with BamH1 or SfiI, before and after ligation with Sau3A or SfiI oligonucleotides.

| Enzyme cleavage | Before ligation | no oligo | Ligation with: SfiI-oligo | Sau3A-oligo |
|---|---|---|---|---|
| BamH1 | 100 | 5 | 5 | 95 |
| SfiI | 100 | 5 | 95 | 5 |

The results show that SfiI and Sau3A oligonucleotides efficiently terminates ligations of pRIT28 cleaved by SfiI and BamHl, respectively. This demonstrates that the oligonucleotides are efficiently and specifically incorporated into the site created by SfiI and BamHl, respectively.

EXAMPLE 3

Solid-Phase DNA Sequencing Using PCR Amplified Templates

Solid-phase sequencing using the concept schematically outlined in FIG. 1 was performed except that the target sequence was amplified by the PCR technique before immobilization by biotin to avidin agarose. Plasmid pRIT27 containing a synthetic human proinuslin gene fragment was transformed in to E.coli strain RR1 M15 and plated on agar medium. A single colony was picked up with a sterilised Pasteur pipette and suspended in 10 ul PCR buffer, consisting of 67 mM Tris-HCl, pH 10.00, 16.6 mM (NH₄)₂SO₄, 6.7 mM MgCl₂, 10 mM β-mercaptoethanol and 170 ug/ml BSA. The sample was heated to 95° C. for 5 min and, after cooling to room temperature, neutralized by the addition of 1 ul of a 10×PCR buffer, pH 7.0.

The PCR was performed with two oligonucleotide primers complimentary to a region upstream, (biotin-CCATGATTACGAATTTAATAC-3') and downstream (5'-TTCGATA TCGGTAACCAGCACT-CCATGTCATGG-3'), respectively, of the multi-linker region. The upstream primer was biotinylated in the 5'-end as described by the manufacturers (Pharmacia, Sweden).

The reaction micture (100 ul) consisted of the above described PCR buffer, pH 8.8, 1 uM each of the primers, 200 uM each of dATP, dCTP, and dTTP and the above described 10 ul of lysed sample. Two units of TaqI-polymerase (Amersham, England) was added and temperature cycle reactions were carried out using a Techne programmable Dri-Block PHC-1 (Techne, UK). Each cycle included a heat denaturation step at 92° C. for 1 min, followed by annealing of primers to the DNA for 2 min at 50° C., and DNA chain extension with TaqI-polymerase for 1 min at 72° C. The reaction mixture were covered with a drop of parafin oil. After 20 cycles, the mixture were added to 20 ul of avidin agarose (as described in example 1). The supernatant was removed and the immobilized doubled stranded DNA was converted into single stranded form by incubation at 37° C. with 0.15M NaOH for 15 min. The avidin agarose, with immobilized template DNA was subsequently washed with 0.15M NaOH and TE-buffer.

Sequencing reactions were performed using a fluorescent end-labelled sequencing primer (5'-CGTTGTAA AACGGCCAGT-3'), complimentary to a region immediately downstream from the multi-linker region. 2 pmole of the sequencing primer were mixed with the avidin agarose immobilized template DNA in a buffer containing 10 mM Tris-HCl (pH 7.5) 10 mM MgCl₂, 100 ug/ml BSA and 100 mM NaCl to a total volume of 10 ul. The annealing mixture was heated at 65° C. and allowed to cool to room temperature. 1 ul DTT/NaCl mixture (0.8M NaCl/0.1M DTT) and 4 units of T7-polymerase (Pharmacia, Sweden) were added and the volume was adjusted to 15 ul. Then 3.5 ul of aliquots of the mixture were mixed with 2.5 ul of respective nucleotide mixture and incubated 10 min at 37° C. The following nucleotide mixtures were used; 80 uM each dATP, dCTP, dGTP, dTTP, 6.3 uM of respective ddNTP, 50 mM NaCl and 40 mM Tris-HCl pH 7.5. When the extension reactions were complete the supernatants of each reactions were removed and the avidin agarose was washed with water. The newly synthesized oligonucleotides were eluted using 3 ul of a formamide/sequencing dye mixture consisting of deionized formamide containing 10 mM EDTA, pH 7.5. After 15 min incubation at 37° C. the supernatant was removed and diluted with 3 ul water. Approx 2 ul were loaded into an automated sequencing apparatus set-up to detect fluroescent bands during electrophoresis (Ansorge et al). A sequencing run with a 20 cm separating length, and 7% polyacrylamide gel, gave clear results. This example illustrates that the solid-phase sequencing can be used for sequencing of PCR amplified DNA using T7 DNA polymerase and a fluorescent primer.

EXAMPLE 4

Solid Phase Sequencing of Genomic DNA Using PCR Amplified Templates on Surface Modefied Microtiter Plates Staphylococcus aureus SA113 was grown as single colonies on TBAB-plates. A single colony was picked with a sterilized Pasteur pipette and suspended in 10 ul PCR buffer, consisting of 67 mM Tris-HCl, pH 10.0, 16.6 mM (NH₄)SO₄, 6.7 mM MgCl₂, 10 mM β-mercaptoethanol and 170 ul/ml BSA. The sample was lysed by heating at 95° C. for 5 min and, after cooling to room temperature, neutralized by the addition of 1 ul of a 10×PCR buffer, pH 7.0.

The PCR was performed with two oligonucleotide primers complimentary to the Staphylococcal protein A gene. One primer was biotinylated at the 5'-end (biotin-AATAGCGTGATTTTGCGGT-3'), the second primer (GACCACCGCATT-GTGGACGTGACCG-GCAGCAAAATG-5'), contains, at the 5'-end, a specif handle sequence not complimentary to the DNA template; this handle sequence creates a primer annealing seuence.

The reaction mixture (100 ul) consisted of the above described PCR buffer, pH 8.8 1 uM each of the primers, 200 uM each of dATP, dCTP, dGTP and dTTP and the above described 10 ul of lysed sample. Two units of TaqI-polymerase (Amersham, England) were added and temperature cycle reactions were carried out using a Techne programmable Dri-Block PHC-1 (Techne, UK). Each cycle included a head denaturation step at 92° C. for 1 min, followed by annealing of primers to the DNA for 2 min at 50° C. and DNA chain extension with TaqI-polymerase for 1 min at 72° C. The reaction mixture was overlaid with a drop of paraffin oil.

Polystyrene microtiter plates (Costar, USA) were surface grafted with 0.2M glycidyl methacrylate and 2M benzophenone, in acetone by UV irradiating for 2 minutes. (K. Almer et.al, Polymer Chamistry 26, 1988, 2099–21110). 25 ug Streptavidin (Amersham, UK) in a TE buffer, at a total volume of 10 ul was applied to each well and the microtiter plate was incubated over night at 42° C. After removing the supernatant, the wells were incubated with BSA, 100 ug/ml in TE-buffer, overnight at a total volume of 10 ul and 42° C. The supernatant was removed and the wells subsequently washed with 1×TE.

After 20 temperature reaction cycles, 10 ul of the mixture were added to each of 4 microtiter wells, prevously treated as above described. After 15 minutes the supernatant was removed and the wells washed with $H_2O$. The immobilized double stranded DNA was converted into single stranded form by incubation at 37° C. with 15 ul 0.15M NaOH. The wells, with immobilized template DNA were subsequently washed with 0.15M NaOH and TE-buffer.

Sequencing reactions were performed using a 32P end-labelled sequencing primer (5'-GTAAAACGG-CCAGT-3'), complimentary to a region immediately downstream from the multi-linker region. 2 pmole of the sequencing primer were mixed with the avidin agarose with immobilized template DNA in a buffer containing 10 mM Tris-HCl (pH 7.5) 10 mM $MgCl_2$, 200 ug ml BSA and 100 mM NaCl at a total volume of 10 ul. The annealing mixture was heated to 65° C. and allowed to cool to room temperature.

The supernatant was removed and 4.2 ul of nucleotide mixture (see below) were added together with 2 ul DTT/NaCl mixture (0.03M DTT/0.25 mM NaCl) and 1 unit of T7-polymerase (Pharmacia, Sweden), in a buffer consisting of 10 mM Tris-HCl (pH 7.5), 10 mM $MgCl_2$, 100 ug/ml BSA and 100 mM NaCl. The volume was adjusted to 10 ul and the microtiter plate were incubated 10 minutes at 37° C.

The following nucleotide mixture was used; 80 uM each of dATP, dCTP, dGTP, dTTP and 6.3 uM of respectively ddNTP and 50 mM NaCl and 40 mM Tris-HCl pH 7.5. After completed extension reactions the supernatant was removed and the microtiter wells were washed with $H_{20}$. The newly synthesized oligonucleotide were eluted using 3 ul of a formamide/sequencing dye mixture consisting of deionized formamide containing 10 mM EDTA, pH 7.5 0.3% (w/v) xylan cyanol FF and 0.3% (w/v) Bromphenol Blue. After 15 min incubation at 37° C. the supernatant was removed and diluted with 3 ul $H_2O$.

Approx. 2 ul were loaded on a seuencing gel, and the resulting autoradiogram showed a clear sequence of the Staphylococcal gene fragment. This example illustrates that the solid phase sequencing approach can be used for direct sequencing of genomic DNA using PCR technology. It also illustrated that plastic microtiter wells with covalently bound streptavidin can be used as a solid support.

REFERENCES

Ansorge, W., Sproat, B., Stegemann, J., Schwager, C. and Zenke, M. (1987) Nuc. Acids Res. 15, 4593–4602

DeBonville, D. A. and G. E. Riedel (1987) In Advances in Laboratory Automation Robotics. 1986. J. R. Strimaitis and G. L. Hawk, eds. Zymark Corp. Hopkinton, Mass. pp. 353–360

Dente, L., Cesarini, G. and Cortese, R. (1983) Nuc. Acids Res. 11, 1645–1655

Elder, J. K., Green, D. K. and Southern, E. M. (1985) Nuc. Acids Res. 14, 417

Kristensen, T., Voss, H. and Ansorge, W. (1987) Nuc. Acids Res. 15, 5507–5515

Maniatis, T., Fritsch, E. F. and Sambrook, J. Molecular Cloning; a laboratory manual. Cold Spring Harbour Laboratory. Cold Spring Harbour, N.Y., 1982

Martin, W. J., Warmington J. R., Galinski, B. R., Gallagher, M., Davies, R. W., Beck, M. S. and Oliver S. G. (1985) Biotechnology 3, 911–915

Olsson, A. and Uhlen, M. (1986) Gene 45, 175–181

Prober, J. M., Trainor, G. L., Dam, R. J., Hobbs, F. W., Robertson, C. W., Zagursky, R. J., Cocuzza, A. J., Jensen, M. A. and Baumeister, k. (1987) Science 238, 336–341

Rosenthal et al, (1985) Nucleic Acids Res. 13, 1173–1184

Sanger, F., Nicklen, S. and Coulson, A. R. (1977) Proc. Natl. Acad. Sci., USA 74, 5463–5467

Smith, L. and Hood, L. (1987) Biotechnology 5, 933–939

Smith, L. M., Sanders, J. Z., Kaiser, R. J., Hughs, P., Dodd, C., Connel, C. R., Heiner, C., Kent, S. B. H. AND Hood, L. (1986) Nature 321, 674–679

Wada, A., Yamaoto, M. and Soeda, E. (1983) Rev. Sci. Instru. 54, 1569–1572

I claim:

1. A method for solid-phase sequencing of one strand of double-stranded DNA comprising the steps of:
   (A) providing said double-stranded DNA;
   (B) immobilizing on a solid support one terminus of one of the two strands of said double-stranded DNA;
   (C) subjecting said immobilized double-stranded DNA to strand separation, thereby providing an immobilized strand and an unattached strand;
   (D) removing said unattached strand, thereby providing an immobilized single-stranded DNA;
   (E) sequencing said immobilized single-stranded DNA.

2. The method of claim 1 wherein strand separation is effected by melting.

3. The method of claim 1 wherein prior to step (B), a functional group which binds to the solid support is introduced at only one terminus of one of the strands of the double stranded DNA.

4. The method of claim 1 wherein the double stranded DNA is a plasmid containing a target sequence; the plasmid is cleaved at a restriction site outside the target sequence; a functional group is introduced at at least one terminus of one strand only of said DNA; the functionality DNA is cleaved at a further restriction site outside the target sequence; and the functionalized target sequence is contacted with a solid support carrying a substance with affinity for said functional group.

5. The method of claim 1 wherein the double stranded DNA is a plasmid containing a target sequence; the plasmid DNA is cleaved at a restriction site outside the target sequence and at one or more restriction sites within the target sequence; and oligonucleotides are ligated at both termini of the plasmid DNA generated by said cleavage, wherein one of said oligonucleotides carries a functional group which binds to a solid support and the other oligonucleotide is capable of hybridizing to a general sequencing primer, 6. The method of claim 1 wherein the immobilized double stranded DNA is produced by the polymerase chain reaction method using at least one oligonucleotide primer carrying means for attachment to a solid support.

7. The method of claim 6 wherein the immobilized double stranded DNA is produced by amplification of genomic DNA by the polymerase chain reaction method.

8. The method of claim 1 wherein said immobilized single stranded DNA is sequenced by the primer extension method, 9. The method of claim 3 wherein said functional group is a biotin, avidin, streptavidin or thiol group and said solid support carries groups binding thereto.

10. The method of claim 1 wherein the solid support is in particulate form or is a microtitre well.

11. The method of claim 1 wherein stand separation is effectuated by treatment with aqueous alkali.

12. The method of claim 9, wherein said functional group is biotin.

13. The method of claim 11 wherein said strand separation is effectuated by treatment with 0.15M NaOH.

* * * * *